(12) United States Patent
Gerwert et al.

(10) Patent No.: US 11,592,451 B2
(45) Date of Patent: *Feb. 28, 2023

(54) METHOD FOR THE PRESELECTION OF DRUGS FOR PROTEIN MISFOLDING DISEASES

(71) Applicant: betaSENSE GmbH, Münster (DE)

(72) Inventors: Klaus Gerwert, Muenster (DE); Andreas Nabers, Markt Schwaben (DE); Jonas Schartner, Herne (DE)

(73) Assignee: betaSENSE GmbH, Münster (DE)

(*) Notice: Subject to any disclaimer, the term of this patent is extended or adjusted under 35 U.S.C. 154(b) by 40 days.

This patent is subject to a terminal disclaimer.

(21) Appl. No.: 16/349,194

(22) PCT Filed: Nov. 21, 2017

(86) PCT No.: PCT/EP2017/079924
§ 371 (c)(1),
(2) Date: May 10, 2019

(87) PCT Pub. No.: WO2018/091738
PCT Pub. Date: May 24, 2018

(65) Prior Publication Data
US 2019/0285650 A1  Sep. 19, 2019

(30) Foreign Application Priority Data
Nov. 21, 2016 (EP) .................. 16199792

(51) Int. Cl.
*G01N 33/68* (2006.01)
*G01N 21/552* (2014.01)
*G01N 21/35* (2014.01)

(52) U.S. Cl.
CPC ....... *G01N 33/6896* (2013.01); *G01N 21/552* (2013.01); *G01N 21/35* (2013.01);
(Continued)

(58) Field of Classification Search
CPC ............. G01N 33/6896; G01N 21/552; G01N 2500/04; G01N 2800/2828;
(Continued)

(56) References Cited

U.S. PATENT DOCUMENTS

| 6,110,446 A | 8/2000 | Prencipe et al. |
| 11,073,470 B2 | 7/2021 | Gerwert et al. |

(Continued)

FOREIGN PATENT DOCUMENTS

| EP | 1214594 | 5/2000 |
| EP | 1806574 | 7/2007 |

(Continued)

OTHER PUBLICATIONS

Piling et al., (2016) "Fundamental developments in infared spectroscopic imaging for biomedical applications", The Royal Society of Chemistry, Chem. Soc. 2016, 45:1935-1957.
(Continued)

*Primary Examiner* — Shafiqul Haq
*Assistant Examiner* — Nam P Nguyen
(74) *Attorney, Agent, or Firm* — Carol L. Francis; Mandar A. Joshi; Bozicevic, Field & Francis LLP (57) ABSTRACT

The invention provides a method that gives direct information about the intervention of a potential drug on the secondary structure distribution of a targetbiomolecule, i.e., for a disease with misfolded protein, such as neurodegenerative diseases in a complex body fluid. The secondary structural change is monitored by vibrational spectroscopy. The method can be applied for prescreening of drug candidates for targeting of specific biomolecules. The effect of the drug on the secondary structure distribution is monitored label-free in real time and provides thereby direct information about the efficacy of the potential drug.

23 Claims, 4 Drawing Sheets

(52) U.S. Cl.
CPC ............... *G01N 2021/3595* (2013.01); *G01N 2333/4709* (2013.01); *G01N 2500/04* (2013.01); *G01N 2800/2821* (2013.01); *G01N 2800/2828* (2013.01); *G01N 2800/2835* (2013.01); *G01N 2800/52* (2013.01)

(58) Field of Classification Search
CPC ........... G01N 2800/2835; G01N 21/35; G01N 2021/3595; G01N 2333/4709; G01N 2800/2821; G01N 2800/52
See application file for complete search history.

(56) References Cited

U.S. PATENT DOCUMENTS

| | | |
|---|---|---|
| 2003/0157725 A1 | 8/2003 | Franzen et al. |
| 2004/0121491 A1 | 6/2004 | Marchand-Brynaert et al. |
| 2004/0180147 A1 | 9/2004 | Parikh et al. |
| 2005/0282925 A1 | 12/2005 | Schlenoff et al. |
| 2009/0028869 A1 | 1/2009 | Dodel et al. |
| 2009/0202515 A1 | 8/2009 | Yoneyama et al. |
| 2012/0021486 A1 | 1/2012 | Dinu et al. |
| 2012/0170023 A1 | 7/2012 | Szobota et al. |
| 2012/0309943 A1 | 12/2012 | Kumada et al. |
| 2013/0022620 A1 | 1/2013 | Schmidt et al. |
| 2014/0288093 A1 | 9/2014 | Krainc et al. |
| 2015/0140003 A1 | 5/2015 | Kaluza et al. |
| 2015/0309045 A1* | 10/2015 | Picotti ..................... C12Q 1/37 506/6 |
| 2016/0279238 A1 | 9/2016 | Neumann et al. |
| 2017/0010212 A1 | 1/2017 | Gerwert et al. |
| 2018/0328835 A1 | 11/2018 | Bauer et al. |
| 2019/0277863 A1 | 9/2019 | Barbour |
| 2019/0285651 A1* | 9/2019 | Gerwert ............. G01N 33/6896 |
| 2019/0369015 A1 | 12/2019 | Ismail et al. |
| 2020/0141864 A1 | 5/2020 | Ismail et al. |
| 2020/0141866 A1* | 5/2020 | Gerwert ................. G01N 21/64 |
| 2020/0240908 A1* | 7/2020 | Gerwert ............. G01N 21/6428 |

FOREIGN PATENT DOCUMENTS

| | | |
|---|---|---|
| EP | 2490029 | 8/2012 |
| EP | 2700933 | 2/2014 |
| JP | 2002040023 | 2/2002 |
| WO | 200070345 | 11/2000 |
| WO | 200201202 | 1/2002 |
| WO | WO 2002/056018 | 7/2002 |
| WO | WO 2007/131997 | 11/2007 |
| WO | WO 2015/121339 | 8/2015 |
| WO | 2018091738 | 5/2018 |
| WO | WO 2018/091743 | 5/2018 |
| WO | 2018/219969 | 12/2018 |

OTHER PUBLICATIONS

Konishi, Eiji, et al., (2010) "Antibodies to Bovine Serum Albumin in Human Sera: Problems and Solutions with Casein-Based ELISA in the Detection of Natural Japanese Encephalitis Virus Infections", Jpn. J. Infect. Dis., 63:296-298.
Nisha Syad, Arif, et al., (2015) "Assessment of anti-arnyloidogenic activity of marine red alga G. acerosa against Alzheimer's beta-amyloid peptide 25-35", Neurological Research, 37(1):14-22.
Xiao, Yuhong, et al., (2012) "Enzyme-Linked Immunosorbent Assay (ELISA) and Blocking with Bovine Serum Albumin (BSA)—Not all BSAs are alike", J. Immunol Methods, 384(1-2):148-151.
Lin et al., (2014) "A Modified Infrared Spectrometer with High Time Resolution and Its Application for Investigating Fast Conformational Changes of the GTPase Ras", Applied Spectroscopy, 68(5):531-535.
Piling et al. (2016) "Fundamental developments in infrared spectroscopic imaging for biomedical applications", The Royal Society of Chemistry, Chem. Soc., 45:1935-1957.
Ahmed et al., (2015) "Berberine and Neurodegeneration: A Review of Literature", Pharmacol. Reports 67(5):970-979.
Akoury et al., (2013) "Mechanistic Basis of Phenothiazine-Driven Inhibition of Tau Aggregation", Angew. Chem. (Int. Ed. Engl.) 52(12):3511-3515.
Alzheimer, (1907) "ALZFORUM Networking for a Cure" Allg. Z. Psychiatrie Psychisch-gerichtl. Med. 64:146-148.
Andreasen et al., (1998) Cerebrospinal Fluid Tau Protein as a Biochemical Marker for Alzheimer's Disease: A Community Based Follow Up Study, J. Neurology, Neurosurgery and Psychiatry 64(3):298-305.
Ataka et al., (2004) "Oriented Attachment and Membrane Reconstitution of His-Tagged Cytochrome c Oxidase to a Gold Electrode: In Situ Monitoring by Surface-Enhanced Infrared Absorption Spectroscopy", JACS Articles 126:16199-16206.
Baddeley et al., (2015) "Complex Disposition of Methylthioninium Redox Forms Determines Efficacy in Tau Aggregation Inhibitor Therapy for Alzheimer's Disease", J Pharm. Exp. Therap. 352(1):110-118.
Badura et al., (2006) "Light-Driven Water Splitting for (Bio-)Hydrogen Production: Photosystem 2 as the Central Part of a Bioelectrochemical Device", Photochemistry and Photobiology 82:1385-1390.
Bard et al., (2003) "Epitope and Isotope Specificities of Antibodies to β-Amyloid Peptide for Protection Against Alzheimer's Disease-like Neuropathology", PNAS 100(4):2023-2028.
Benilova et al., (2012) "The Toxic Aβ Oligomer and Alzheimer's Disease: An Emperor in Need of Clothes", Nature Neuroscience 15(3):349-357.
Bennett et al., (2004) "Neurofibrillary Tangles Mediate the Association of Amyloid Load With Clinical Alzheimer Disease and Level of Cognitive Function", Arch. Neurol. 61(3):378-84.
Blennow et al., (2009) "Evolution of Aβ42 and Aβ40 Levels and Aβ42/Aβ40 Ratio in Plasma During Progression of Alzheimer's Disease: A Multicenter Assessment", J Nutr Health Aging, 13(3):205-8.
Braak and Braak, (1991) "Neuropathological Stageing of Alzheimer-Related Changes", Acta Neuropathologica 82(4):239-59.
Brauns and Dyer (2005) "Time-Resolved Infrared Spectroscopy of RNA Folding", Biophysical Journal 89:3523-3530.
Bruggink et al., (2013) "Amyloid-β Oligomer Detection by ELISA in Cerebrospinal Fluid and Brain Tissue", Analytical Biochemistry 433:112-120.
Byrne et al., (2009) "Antibody-Based Sensors: Principles, Problems and Potential for Detection of Pathogens and Associated Toxins", Sensors 9:4407-4445.
Campisi et al., (2011) "Effect of Berberine and Berberis Aetnensis C. Presl. Alkaloid Extract on Glutamate-Evoked Tissue Transglutaminase Up-Regulation in Astroglial Cell Cultures", Phytotherapy Res. 25(6):816-820.
Cavallucci et al., (2012) "Aβ Toxicity in Alzheimer's Disease", Mol. Neurobiol. 45:366-378.
Cedernaes et al., (2014) "Efficacy of Antibody-Based Therapies to Treat Alzheimer's Disease: Just a Matter of Timing?", Exp. Geront. (57)104-106.
Cerf et al., (2009) "Antiparallel β-Sheet: A Signature Structure of the Oligomeric Amyloid β-Peptide", Biochem. J. 421:415-423.
Chiba (2013) "Emerging Therapeutic Strategies in Alzheimer's Disease", Neurodegenerative Diseases 181-225.
Coomaraswamy et al., (2010) "Modeling Familial Danish Dementia in Mice Supports the Concept of the Amyloid Hypothesis of Alzheimer's Disease", PNAS 107(17):7969-7974.
Cummings (2011) "Biomarkers in Alzheimer's Disease Drug Development", Alzheimer's & Dementia 7(3):e13-44.
Devouge et al., (2005) "A Practical Molecular Clip for Immobilization of Receptors and Biomolecules on Devices' Surface: Synthesis, Grafting Protocol and Analytical Assay", Bioorganic & Medicinal Chemistry Letters 15:3252-3256.
Devouge et al., (2009) "Surface Functionalization of Geranium ATR Devices for use in FTIR-Biosensors", Journal of Colloid and Interface Science 332(2): 408-415.
Doecke et al., (2012) "Blood-Based Protein Biomarkers for Diagnosis of Alzheimer Disease", Arch. Biol. 69(10):1318.

(56) References Cited

OTHER PUBLICATIONS

Elfrink et al., (2007) "Interaction of the Cellular Prion Protein with Raft-like Lipid Membranes", Biol. Chem. 388:79-89.

Elfrink et al., (2008) "Structural changes of membrane-anchored native PrP$^c$", PNAS 105 (31): 10815-10819.

Emre (2002) "Switching Cholinesterase Inhibitors in Patients with Alzheimer's Disease", Int. J. Clinical Practice Supplement 127:64-72.

Evora (2016) Methylene Blue Is a Guanylate Cyclase Inhibitor That Does Not Interfere with Nitric Oxide Synthesis, Texas Heart Institute Journal 43(1):103.

Fändrich, et al., (2009) "Structural Polymorphism of Alzheimer Aβ and Other Amyloid Fibrils", Prion, Landes Bioscience 3(2):89-93.

Fiandaca et al., (2015) "Plasma 24-Metabolite Panel Predicts Preclinical Transition to Clinical Stages of Alzheimer's Disease", Frontiers in Neurology 6(237):1-13.

Fjorback et al., (2007) "Determination of α-Synuclein Concentration in Human Plasma Using ELISA", Scand. J. Clin. Lab. Invest. 67:431-435.

Frost et al., (2009) "Conformational Diversity of Wild-type Tau Fibrils Specified by Templated Conformation Change*", The Journal of Biological Chemistry 284 (6): 3546-3551.

Funke et al., (2005) "A Unique Sequence Motif in the 54-kDa Subunit of the Chloroplast Signal Recognition Particle Mediates Binding to the 43-kDa Subunit*", The Journal of Biological Chemistry 280(10):8912-8917.

Funke et al., (2010) "Single-Particle Detection System for Aβ Aggregates: Adaptation of Surface-Fluorescence Intensity Distribution Analysis to Laser Scanning Microscopy", Rejuvenation Research 13 (2-3): 206-209.

Funke (2011) "Detection of Soluble Amyloid-β Oligomers and Insoluble High-Molecular-Weight Particles in CSF: Development of Methods with Potential for Diagnosis and Therapy Monitoring of Alzheimer's Disease", International Journal of Alzheimer's Disease 8 pages.

Gabelle et al., (2011) "Decreased sAβPPβ, Aβ38, and Aβ40 Cerebrospinal Fluid Levels in Frontotemporal Dementia", J Alzheimers Dis., 26(3):553-563.

Glabe (2008) "Structural Classification of Toxic Amyloid Oligomers", J. Biol. Chem. 283(44):29639-29643.

Goldzstein et al., (2009) "Ligand-Receptor Interactions in Complex Media: A New Type of Biosensors for the Detection of Coagulation Factor VIII", Biosensors and Bioelectronics 24:1831-1836.

Goldzstein (2012) "Development of a New Type of Biosensors Based on ATR-FTIR Spectroscopy", pp. 111-113.

Greenberg et al., (2013) "Improving Alzheimer's Disease Phase II Clinical Trials", Alzheimer's & Dementia 9(1):39-49.

Güldenhaupt et al., (2008) "Secondary Structure of Lipidated Ras Bound to a Lipid Bilayer FEBS", Journal 275 (23):5910-5918.

Haass and Selkoe, (2007) "Soluble Protein Oligomers in Neurodegeneration: Lessons from the Alzheimer's Amyloid β-peptide", Nature Rev. Mol. Cell Biol. 8(2):101-112.

Habicht et al., (2007) "Directed Selection of a Conformational Antibody Domain that Prevents Mature Amyloid Fibril Formation by Stabilizing Aβ Protofibrils", PNAS 104(49): 19232-19237.

Han et al., (2001) "Formation of Alkanethiol Monolayer on Ge(111)", J. Am. Chem. Soc. 123:2422-2425.

Harrington et al., (2015) "Cellular Models of Aggregation-Dependent Template-Directed Proteolysis to Characterize Tau Aggregation Inhibitors for Treatment of Alzheimer Disease*", J. Biol. Chem. 290(17):10862-10875.

Heiser et al., (2000) "Inhibition of Huntingtin Fibrillogenesis by Specific Antibodies and Small Molecules: Implications for Huntington's Disease Therapy", PNAS 97(12): 6739-6744.

Hofer and Fringeli (1979) "Structural Investigation of Biological Material in Aqueous Environment by Means of Infrared-ATR Spectroscopy", Biophys. Struct. Mech. 6:67-80.

Hülsemann et al., (2016) "Biofunctionalized Silica Nanoparticles: Standards in Amyloid-β Oligomer-Based Diagnosis of Alzheimer's Disease", J. Alzheimer's Disease. 54:79-88.

Imbimbo (2009) "Why Did Tarenflurbil Fail in Alzheimer's Disease?", J. Alzheimer's Disease: JAD 17(4):757-760.

Klieren et al., (2010) "Development of a Quantitative and Conformation-Sensitive ATR-FTIR Biosensor for Alzheimer's Disease: The Effect of Deuteration on the Detection of the Aβ Peptide", Spectroscopy 24: 61-66.

Klieren et al., (2013) "Towards an Early Diagnosis of Alzheimer's Disease: Development of an ATR-FTIR Biosensor for the Detection of Aβ Toxic Conformations", ULB ECOLE Interfacultaire De Bioingenieur 161 pages.

Kolarova et al., (2012) "Structure and Pathology of Tau Protein in Alzheimer Disease", Int. J. Alzheimer's Disease pp. 1-13.

Kötting et al., (2012) "Time-Resolved FTIR Spectroscopy for Monitoring Protein Dynamics Exemplified by Functional Studies of Ras Protein Bound to a Lipid Bilayer", Chemical Physics 396:72-83.

Kötting and Gerwert (2005) "Proteins in Action Monitored by Time-Resolved FTIR Spectroscopy", ChemPhysChem 6:881-888.

Kühbach et al., (2016) "Application of an Amyloid Beta Oligomer Standard in the sFIDA Assay", Frontiers in Neuroscience 10(8):1-6.

Laganowsky et al., (2012) "Atomic View of a Toxic Amyloid Small Oligomer", Science 335(6073): 1228-1231.

Lee et al., (2001) "Neurodegenerative Tauopathies: Human Disease and Transgenic Mouse Models", Annual Rev. of Neuroscience 24:1121-1159.

Lee et al., (2012) "Phellodendron Amurense and Its Major Alkaloid Compound, Berberine Ameliorates Scopolamine-Induced Neuronal Impairment and Memory Dysfunction in Rats", Korean J. Physiol. & Pharmacol. 16(2):79-89.

Lo et al., (2011) "Longitudinal Change of Biomarkers in Cognitive Decline", Arch. Neurol. 68(10):1257-1266.

Löfås and Johnson (1990) "A Novel Hydrogel Matrix on Gold Surfaces in Surface Plasmon Resonance Sensors for Fast and Efficient Covalent Immobilization of Ligands", J. Chem. Soc., Chem. Commun. pp. 1526-1528.

Loscutoff and Bent (2006) "Reactivity of the Geranium Surface: Chemical Passivation and Functionalization", Annu. Rev. Phys. Chem. 57:467-495.

Mapstone et al., (2014) "Plasma Phospholipids Identify Antecedent Memory Impairment in Older Adults", Nature Medicine 20(4):415-418.

Matijašević et al., (2008) "In Situ ATR FTIR Monitoring of the Formation of Functionalized Mono- and Multilayers on Germanium Substrate: from 7-Octenyltrichlorosilane to 7-Carboxylsilane", Langmuir 24:2588-2596.

Morgado et al., (2012) "Molecular Basis of β-Amyloid Oligomer Recognition with a Conformational Antibody Fragment", Proceedings of the Nat'l Academy of Sciences 109(31): 12503-12508.

Nabers et al., (2016) "Amyloid-β-Secondary Structure Distribution in Cerebrospinal Fluid and Blood Measured by an Immuno-Infrared-Sensor: A Biomarker Candidate for Alzheimer's Disease", Anal. Chem. 88(5):2755-2762.

Nabers et al., (2016) "An Infrared Sensor Analysing Label-Free the Secondary Structure of the Aβ Peptide in Presence of complex Fluids", J. Biophotonics 9(3):224-234.

Necula et al., (2007) "Methylene Blue Inhibits Amyloid Aβ Oligomerization by Promoting Fibrillization", Biochem. 46(30):8850-8860.

Ollesch et al., (2007) "Prion Protein α-to-β Transition Monitored by Time-Resolved Fourier Transform Infrared Spectroscopy", Society for Applied Spectroscopy 61(10): 1025-1031.

Ollesch et al., (2013) "FTIR Spectroscopy of Biofluids Revisited: An Automated Approach to Spectral Biomarker Identification", Analyst 138:4092-4102.

Olstynska-Janus et al., (2012) "Spectroscopic Techniques in the Study of Human Tissues and their Components. Part I: IR Spectroscopy", ACTA of Bioengineering and Biomechanics Review Article 14(3):101-115.

Perchiacca et al., (2012) "Structure-Based Design of Conformation- and Sequence-Specific Antibodies Against Amyloid β", PNAS 109(1):84-89.

(56) References Cited

OTHER PUBLICATIONS

Pickhardt et al., (2015) "Identification of Small Molecule Inhibitors of Tau Aggregation by Targeting Monomeric Tau as a Potential Therapeutic Approach for Tauopathies", Current Alzheimer Res. 12(9):814-828.
Pinkerneil et al., (2012) "Surface-Attached Polyhistidine-Tag Proteins Characterized by FTIR Difference Spectroscopy", Chem Phys Chem 13 (11): 2649-2653.
Prince et al., (2015) "World Alzheimer Report 2015 The Global Impact of Dementia an Analysis of Prevalence, Incidence, Cost and Trends", Alzheimer's Disease International 87 pages.
Product Information (2018) "Anti-β-Amyloid (13-28) Antibody, Mouse Monoclonal", Immunohistochemistry Western Immunoprecipitation Sigma-Aldrich A8978:1-4.
Punzet et al., (2012) "Determination of Surface Concentrations of Individual Molecule-Layers used in Nanoscale Biosensors by in Situ ATR-FTIR Spectroscopy", Nanoscale 4:2431-2438.
Ramsay et al., (2007) "Methylene Blue and Serotonin Toxicity: Inhibition of Monoamine Oxidase A (MAO A) Confirms a Theoretical Prediction", British J. Pharmacol. 152(6):946-951.
Rey-Funes et al., (2016) "Methylene Blue Prevents Retinal Damage in an Experimental Model of Ischemic Proliferative Retinopathy", Am. J. Physiol., Regulatory, Integrative and Comparative Physiology 310: R1011 -R1019.
Sachse et al., (2008) "Paired β-Sheet Structure of an Aβ(1-40) Amyloid Fibril Revealed by Electron Microscopy", PNAS 105(21):7462-7466.
Sarroukh et al., (2011) "Transformation of Amyloid β(1-40) Oligomers into Fibrils is Characterized by a Major Change in Secondary Structure", Cell. Mol. Life Sci. 68(8):1429-1438.
Schartner et al., (2013) "Universal Method for Protein Immobilization on Chemically Functionalized Germanium Investigated by ATR-FTIR Difference Spectroscopy", JACS 135 (10):4079-4087.
Schartner et al., (2014) "Immobilization of Proteins in their Physiological Active State at Functionalized Thiol Monolayers on ATR-Geranium Crystals", Chembiochem 15(17):2529-2534.
Šimić et al., (2016) "Tau Protein Hyperphosphorylation and Aggregation in Alzheimer's Disease and Other Tauopathies, and Possible Neuroprotective Strategies", Biomolecules 6(6):1-28.
Smith et al., (2004) "Covalent Attachment of a Nickel Nitrilotriacetic Acid Group to a Germanium Attenuated Total Reflectance Element", Langmuir 20:1184-1188.
Syad & Devi (2015) "Assessment of Anti-Amyloidogenic Activity of Marine Red Alga G. Acerosa Against Alzheimer's Beta-Amyloid Peptide 25-35", Neurological Research 37(1):14-22.
Thal et al., (2000) "Sequence of Ab-Protein Deposition in the Human Medial Temporal Lobe", J. Neuropath. Exp. Neurol. 59(8):733-748.
Thal et al., (2006) "The Development of Amyloid β Protein Deposits in the Aged Brain", Sci. Aging Knowl. Environ. Issue, re1:1-12.
Thorsett and Latimer (2000) "Therapeutic Approaches to Alzheimer's Disease", Current Opinion Chem. Biol. 4(4):377-382.
Van Cauwenberge et al., (2012) "Development of a New Low-Cost and Regenerable Detection Device for Microbial Compounds "MIC-ATR"", SSD Health & Environment 112 pages.
Venkataramani et al., (2012) "Antibody 9D5 Recognizes Oligomeric Pyroglutamate Amyloid-β in a Fraction of Amyloid-β Deposits in Alzheimer's Disease without Cross-Reactivity with other Protein Aggregates", Journal of Alzheimer's Disease 29: 361-371.
Voue et al., (2007) "Biochemical Interaction Analysis on ATR Devices: A Wet Chemistry Approach for Surface Functionalization", Langmuir, American Chemical Society 23(2): 949-955.
Wang and Mandelkow (2016) "Tau in Physiology and Pathology", Nature Rev. Neuroscience 17(1):5-21.
Wang-Dietrich et al., (2013) "The Amyloid-β Oligomer Count in Cerebrospinal Fluid is a Biomarker for Alzheimer's Disease", Journal of Alzheimer's Disease 34:985-994.
Wiltfang et al., (2007) "Amyloid β Peptide Ratio 42/40 but not Aβ42 Correlates with Phospho-Tau in Patients with Low- and High-CSF Aβ40 Load", J Neurochem 101(4):1053-1059.
Wischik et al., (1996) "Selective Inhibition of Alzheimer Disease-like Tau Aggregation by Phenothiazines", PNAS 93(20):11213-11218.
Wischik et al., (2015) "Tau Aggregation Inhibitor Therapy: An Exploratory Phase 2 Study in Mild or Moderate Alzheimer's Disease", J. Alzheimer's Disease 44:705-720.
Yang et al., (2005) "Tau Protein Aggregation in the Frontal and Entorhinal Cortices as a Function of Aging", Devel. Brain Res. 156(2):127-138.
Yao et al., (2015) "Learning from Berberine: Treating Chronic Diseases through Multiple Targets", Science China Life Sciences 58(9):854-859.
Yu et al., (2009) "Structural Characterization of a Soluble Amyloid β-Peptide Oligomer", Biochemistry 48: 1870-1877.
Zhu and Qian (2006) "Berberine Chloride can Ameliorate the Spatial Memory Impairment and Increase the Expression of Interleukin-1beta and Inducible Nitric Oxide Synthase in the Rat Model of Alzheimer's Disease", BMC Neuroscience 7(78): 1-9.
BioLegend, Product Data Sheet, "Purified anti-a-Synuclein, 103-108", (2015), 2 pages.
Eurogentec, "2011 Price List", Covance Antibodies, https://www.yumpu.com/en/document/read/8051743/2011-price-list-covance-antibodies-eurogentec, (2011), p. 2.
Skibinski and Finkbeiner, Drug discovery in Parkinson's disease—Update and developments in the use of cellular models, Int J High Throughput Screen. ; 2011(2): 15-25.
Giehm et al. (2010) "Strategies to Increase the Reproducibility of Protein Fibrillization in Plate Reader Assays" Analytical Biochemistry 400:270-281.
Stefan Barghorn et al., Tau Paired Helical Filaments from Alzheimer's Disease Brain and Assembled in Vitro Are Based on β-Structure in the Core Domain, Biochemistry, Jan. 16, 2004, 43, 1694-1703.
Koetting et al., (2010) "Label-Free Screening of Drug-Protein Interactions by Time-Resolved Fourier Transform Infrared Spectroscopic Assays Exemplified by Ras Interactions" Applied Spectroscopy, 64:9 967-972.
Lee et al., (1999) "Neurodegenerative Taupathies: Human Disease and Transgenic Mouse Models", vol. 24, pp. 507-510.
NPL search history (2020) 1 page.
Weida and Yee, (2011) "Quantum cascade laser based replacement for FTIR microscopy." Pro. SPIE 7902, Imaging, Manipulation, and Analysis of Biomolecules, Cells, and Tissues IX, 79021C.
Meredith (2005) "Protein Denaturation and Aggregation; Cellular Responses to Denatured and Aggregated Proteins", Ann. N.Y. Acad. Sci., 1066:181-221.
Payne et al. (1988) "Fourier Transform IR Spectroscopy of Collagen and Gelatin Solutions: Deconvolution of the Amide I Band for Conformational Studies", Biopolymers, 27:1749-1760.

\* cited by examiner

METHOD FOR THE PRESELECTION OF DRUGS FOR PROTEIN MISFOLDING DISEASES

The invention provides a method that gives direct information about the intervention of a potential drug on the secondary structure distribution of a target biomolecule, i.e., for a disease with misfolded proteins, such as many neurodegenerative diseases, by monitoring a secondary structural change by vibrational spectroscopy. The method can be applied for prescreening of drug candidates targeting specific biomolecules. The intervention of the drug is monitored label-free in real time and provides direct information about the efficacy of the potential drug to prevent pathological folding species.

BACKGROUND OF THE INVENTION

For example, treatment of Alzheimer's disease (AD) is an emerging field, which affects millions of human beings worldwide. The disease progression is characterized by the formation of plaques and tangles in the brain, which are based on aggregation processes of the Aβ peptide and Tau protein. The protein aggregation is driven by structural transition into β-sheet enriched peptides or protein species. The drug development against the Alzheimer's disease is challenging. Many promising drug candidates failed in the clinical trials (Emre, Int. J. Clinical Practice Supplement 127(June):64-72 (2002); Imbimbo, J. Alzheimer's Disease: JAD 17(4):757-60 doi:10.3233/JAD-2009-1092 (2009); Cummings, Alzheimer's & Dementia 7(3):e13-44 doi: 10.1016/j.jalz.2010.06.004 (2011); Greenberg et al., Alzheimer's & Dementia 9(1):39-49 doi:10.1016/j.jalz.2012.02.002 (2013); Cedernaes et al., Exp. Geront. 57(September):104-6 doi:10.1016/j.exger.2014.05.002 (2014)) and until now no drug is available on the market to cure early/mid stages of Alzheimer's disease nor the late stages. In these stages at which clinical symptoms appear the brain is already irreversible damaged. Therefore, an early diagnosis before clinical symptoms appear is a prerequisite. Such diagnostic tool is patented (previous patent application WO 2015121339). The patent application here shows that this tool can be used to monitor also the intervention of a drug on the secondary structure distribution and its ability to refold the pathological species into harmless forms and monitor thereby its efficacy. Techniques like surface plasmon resonance (SPR), surface acoustic waves (SAW) or quartz crystal microbalance (QCM) are used to analyze protein-ligand or protein drug interactions. Since, these techniques only provide kinetical information, but no spectral or structural resolution; they are not able to monitor secondary structure distributions of proteins. A related approach is the use of high-throughput chemical microarray surface plasmon resonance (HT-CM-SPR), which is in principle a reversed SPR system, because the potential drugs are immobilized and the target protein is flushed over the surface (Pickhardt et al., Current Alzheimer Res. 12(9):814-28 (2015)). This approach was successfully employed to identify small molecules that bind to monomeric Tau (Pickhardt et al., Current Alzheimer Res. 12(9):814-28 (2015)), but an effect on the secondary structure cannot be detected due to the lack of spectral and structural resolution. Further techniques like surface enhanced Infrared absorption (SEIRA) spectroscopy provide spectral resolution, but the reproducibility of the measurements is very challenging due to the preparation of the rough gold surfaces and thus does not provide a robust platform for a protein-drug analysis.

The state of the art in the clinical diagnostics are Positron emission tomography (PET) and Magnetic resonance tomography (MRT) to detect aggregates (accumulated from β-sheet enriched proteins) such as plaques in the human brain. The drug induced dissociation of such aggregates appearing at late stages can be monitored. Nevertheless, PET and MRT are very expensive and time-consuming techniques, which cannot be employed as mass screening method nor for preselection of drug candidates. A further disadvantage is in the case of PET the usage of contrast agents, which also stress the patients. However, these techniques provide the analysis of a drug effect in vivo at later stages of the disease. The presented invention is able to reveal the drug effect by analysing body fluids as shown here for cerebrospinal fluid (CSF). Besides the already mentioned techniques, fluorescence based immuno assays are also an emerging field, especially Enzyme Linked Immunosorbent Assay (ELISA) and surface-based fluorescence intensity distribution analysis (sFIDA). However, in contrast these assays are not label-free as the invention, because the need of fluorescent labelled antibodies which may influence the secondary structure distribution of the target protein (Hülsemann et al., J. Alzheimer's Disease: JAD, July doi:10.3233/JAD-160253 (2016); Kühbach et al., Frontiers in Neuroscience 10:8 doi:10.3389/fnins.2016.00008 (2016)). Most importantly, ELISA and sFIDA do not provide direct information about the secondary structure distribution or changes of the secondary structure distribution by the drug. But this information is crucial for the analysis of a drug effect as for example in neurodegenerative diseases. Common assays like Western blots also require labelled secondary antibodies and provide indirect information on the aggregation state of the protein based on the molecular weight only. Due to the preparation process of the Western blot the native secondary structure of the protein is lost. Thus ELISA, sFIDA, or Western blots are not able to measure directly the intervention of a potential drug on the secondary structure distribution of a target protein. The presented invention overcomes all the mentioned limitations and provides evidence on the drug efficacy in vitro. Detailed information about the surface chemistry and the general set-up is described in the literature by our self (Guldenhaupt et al., FEBS Journal 275 (23): 5910-18 doi:10.1111/j.1742-4658.2008.06720.x (2008); Pinkerneil et al., ChemPhysChem 13 (11): 2649-53 doi: 10.1002/cphc.201200358 (2012); Schartner et al., JACS 135 (10):4079-87 doi:10.1021/ja400253p (2013); Schartner et al., Chembiochem 15(17):2529-34 doi:10.1002/cbic.201402478 (2014); Nabers et al., J. Biophotonics 9(3): 224-34 doi:10.1002/jbio.201400145 (2016); Nabers et al., Anal. Chem. 88(5):2755-62 doi:10.1021/acs.analchem.5b04286 (2016)) and in the patent application WO 2015121339.

As an example for a drug candidate methylene blue is used. It is a compound that is applied in many different scientific fields (Ramsay et al., British J. Pharmacol. 152 (6):946-51 doi:10.1038/sj.bjp.0707430 (2007); Evora, Texas Heart Institute Journal/from the Texas Heart Institute of St. Luke's Episcopal Hospital, Texas Children's Hospital 43(1): 103 doi:10.14503/THIJ-15-5629 (2016); Rey-Funes et al., Am. J. Physiol., Regulatory, Integrative and Comparative Physiology, March, doi:10.1152/ajpregu.00266.2015 (2016)). The aggregation of the Tau protein is associated with several diseases such as Alzheimer's disease (AD), Huntigton disease (HD), or Pick disease (PiD) (Wang and Mandelkow, Nature Rev. Neuroscience 17(1):5-21 doi: 10.1038/nrn.2015.1 (2016); Lee et al., Annual Rev. of Neuroscience 24:1121-59 doi:10.1146/annurev.neuro.24.1.1121

Figure 1:
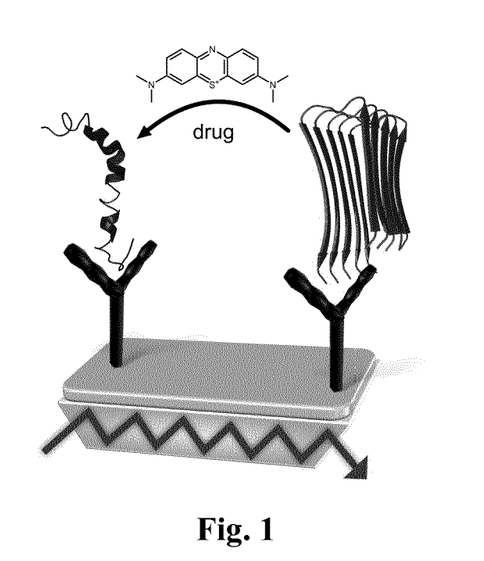
FIG. 1: Graphical abstract showing the general principle of the invented method.
Figure 3:
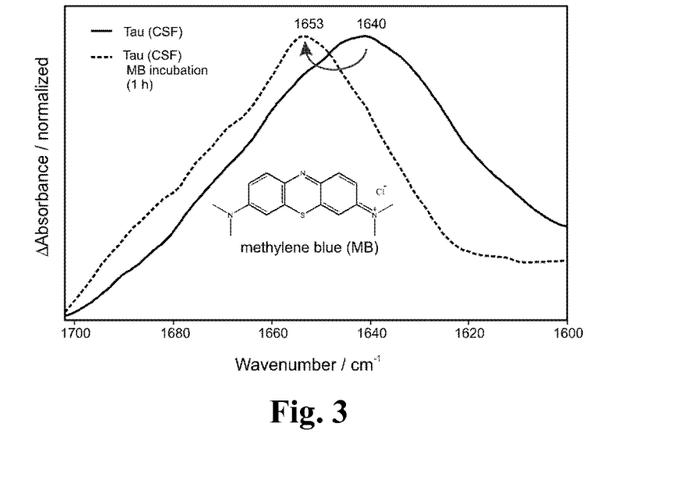
FIG. 3: The Tau protein was immobilized on antibody terminated germanium. The amide I of the Tau protein represents a high amount of β-sheets resulting in an absorbance maximum at 1640 cm$^{-1}$ (black). Addition of the potential drug methylene blue shifted the amide I band to 1653 cm$^{-1}$ indicating a major structural change to α-helix dominated secondary structure distribution (grey).

(2001); Alzheimer, Allg. Z. Psychiatrie Psychisch-gerichtl. Med. 64:146-148 (1907)). Claude Wischik showed in 1996 the selective inhibition of the Tau protein aggregation by methylene blue (Wischik et al., PNAS 93(20):11213-18 (1996)). In the last decades methylene blue was then investigated in several studies and is nowadays analyzed in a clinical phase III trial (Baddeley et al., J. Pharm. Exp. Therap. 352(1):110-18 doi:10.1124/jpet.114.219352 (2015); Harrington et al., J. Biol. Chem. 290(17):10862-75 doi: 10.1074/jbc.M114.616029 (2015); M et al., J. Alzheimer's Disease 2:705-720. doi:10.3233/JAD-142874 (2015); Šimić et al., Biomolecules 6(1):6 doi: 10.3390/biom6010006 (2016)). In 2013 the oxidation of the Cys residue was found to be the mechanistic reason for the inhibition of Tau aggregation (Akoury et al., Angew. Chem. (Int. Ed. Engl.) 52(12):3511-15 doi:10.1002/anie.201208290 (2013)). We here describe a screening method utilizing an ATR-FTIR sensor that measures directly and label-free the effect of potential drugs on the secondary structure distribution of disease related target proteins as schematically shown in FIG. 1. A requirement for the assay is the secondary structural change within the protein during the disease progression. Many neurodegenerative diseases ideally fulfil this requirement, because the disease progression is often characterized by aggregation of a specific protein or peptide. Since, the most common cause of dementia is Alzheimer's disease, we investigated the drug interaction with the two major biomarkers Tau and $A\beta_{1-42}$. In case of the Tau protein, which is involved in the formation of neurofibrillary tangles in the brain of AD patients, methylene blue is a promising drug that is currently evaluated in clinical phase III trial (Wischik et al., PNAS 93(20):11213-18 (1996); Wischik et al., J. Alzheimer's Disease 2:705-720 doi:10.3233/JAD-142874 (2015); Šimić et al., Biomolecules 6(1):6 doi:10.3390/biom6010006. (2016)). We demonstrated the potential of our screening method using two different drug candidates methylene blue and berberine. The intervention of methylene blue on the secondary structure distribution of the human Tau protein extracted from CSF from AD patients was measured (FIG. 3). The potential drug berberine is a multiple target drug that originally comes from traditional Chinese medicine (Yao et al., Science China Life Sciences 58(9):854-59 doi:10.1007/s11427-013-4568-z (2015)). The broad usage of berberine in medical applications is nicely summarized in the review by Ahmed et al. (Ahmed et al., Pharmacol. Reports 67(5):970-79 doi:10.1016/j.pharep.2015.03.002 (2015)). Especially, in the treatment of AD berberine shows promising effects (Ahmed et al., Pharmacol. Reports 67(5):970-79 doi: 10.1016/j.pharep.2015.03.002 (2015); Campisi et al., Phytotherapy Res. 25(6):816-20 doi:10.1002/ptr.3340 (2011); Zhu and Qian, BMC Neuroscience 7:78 doi:10.1186/1471-2202-7-78 (2006); Lee et al., Korean J. Physiol. & Pharmacol. 16(2):79-89 doi: 10.4196/kjpp.2012.16.2.79 (2012)). Berberine shows a positive effect on the memory function in rat models (Lee et al., Korean J. Physiol. & Pharmacol. 16(2):79-89 doi:10.4196/kjpp.2012.16.2.79 (2012); Zhu and Qian, BMC Neuroscience 7:78 doi:10.1186/1471-2202-7-78 (2006); Ahmed et al., Pharmacol. Reports 67(5):970-79 doi:10.1016/j.pharep.2015.03.002 (2015)). Due to the broad spectrum of treatment by berberine, there are many pathways and receptors that might play a crucial role (Ahmed et al., Pharmacol. Reports 67(5):970-79 doi:10.1016/j.pharep.2015.03.002. (2015)). The molecular mechanism on the memory effect that could be important in AD treatment is not completely understood so far.

On the other hand, methods for analyzing the secondary structure distribution of a specific protein in bodily fluids are known in the art. In said methods, the protein of interest is selectively bound within the surface layer, which is achieved with an antibody-functionalized internal reflection element (IRE) (Schartner et al., JACS 135(10):4079-87 doi:10.1021/ja400253p (2013)). This method was applied for the extraction and determination of the secondary structure distribution of the soluble AB fraction from CSF and blood plasma for moderate AD and disease control differentiation (Nabers et al., J. Biophotonics 9(3):224-34 doi:10.1002/jbio.201400145 (2016); Nabers et al., Anal. Chem. Doi: 10.1021/acs.analchem.5b04286 (2016)). WO 2015/121339 provides a biosensor for conformation and secondary structure analysis, notably for the direct non-invasive qualitative secondary structure analysis of a single selected protein within a complex mixture, as e.g. a body fluid, by vibrational spectroscopic methods. For the analysis it is not required that the selected substance is isolated, concentrated, or pretreated by a special preparative procedure. The biosensor is suitable for the determination of a disease, in which a conformational transition of a candidate biomarker protein is associated with disease pathology, wherein a shift of the amide I band maximum of the biomarker protein is indicative for the disease. It is moreover emphasized that such biosensor could potentially also be used to monitor the therapeutic efficacy of drug candidates which support the refolding of Aβ back to the less neurotoxic α-helical form (Nabers et al., Anal. Chem. Doi: 10.1021/acs.analchem.5b04286 (2016)).

It was now found that—with such sensor and with an appropriate assay setting—an intervention of berberine on the $A\beta_{1-42}$ secondary structure distribution in a complex body fluid, which closely resembles the Aβ situation in vivo, can in fact be observed. In particular, we found that berberine decelerates the auto-induced fibrilization of $A\beta_{1-42}$ at high concentrations and may therefore be an interesting drug candidate for further investigations. The two examples show that the ATR-FTIR sensor can be used as an universal in-vitro screening assay in complex bodily fluids to preselect potential drugs for the treatment of neurodegenerative diseases, especially Alzheimer's disease.

SHORT DESCRIPTION OF THE INVENTION

The present invention provides a screening assay utilizing an infrared sensor element for the direct analysis of potential drugs inducing a secondary structural change in the target protein (hereinafter also referred to as "biomarker", "candidate biomarker" and "candidate biomarker protein") that correlates with the efficacy of the drug. It is based on a chemically modified (for example silanes or thiols) germanium surface, which is terminated with covalently attached antibodies. The principle is universal, thus any capture antibody against a desired target protein can be applied and furthermore also any potential drug (small molecule, therapeutic antibody) can be in principle screened with the developed assay. Target proteins can be either immobilized from purified samples or be extracted out of a complex fluid like human CSF. The analysis of the potential drug is done in real-time, label-free and gives evidence of the efficacy in vitro. The invention thus provides (1) a drug-screening assay for determining the efficacy of a potential drug on a target protein undergoing secondary structural changes into a pathological species in a protein misfolding disease (hereinafter also referred to as "disease with misfolded protein"), preferably said assay being performed on a sample derived from a complex body fluid, comprising the steps:

(a) conducting, in an IR cell comprising an infrared sensor element having an internal reflection element with a core of an infrared transparent material and at least one receptor for the candidate biomarker directly grafted to at least one surface of said core, a flux of a sample with soluble candidate biomarker protein, submitting an IR beam through said first IR cell, and obtaining an infrared spectrum therefrom;

(b) conducting, in the same IR cell of step (a), wherein the receptors for the candidate biomarker, which are grafted to the surface of the core, are loaded with the candidate biomarker protein, a flux of a solution with potential drug, submitting an IR beam through said IR cell, and obtaining an infrared spectrum therefrom; and (c) analyzing the obtained infrared spectra to evaluate the effect of the potential drug by determining the secondary structure distribution of the soluble candidate biomarker protein in the sample and after application of the potential drug, preferably an upshift or disappearance of the amide I band in the spectrum of (b) relative to (a) is indicative for the efficacy of the potential drug, and (2) the use of an infrared sensor element as defined in (1) above for the direct analysis of the interaction between a potential drug and a candidate biomarker protein undergoing conformational transitions associated with a disease.

DETAILED DESCRIPTION OF THE INVENTION

The invention describes a method for the preselection of potential drugs against pathological misfolded protein targets, such as in many neurodegenerative diseases. The method comprises the steps:

(a) conducting, in an IR cell comprising an infrared sensor element having an internal reflection element with a core of an infrared transparent material and at least one receptor for the candidate biomarker directly grafted to at least one surface of said core, a flux of a sample with soluble candidate biomarker protein, submitting an IR beam through said first IR cell, and obtaining an infrared spectrum therefrom;

(b) conducting, in the same IR cell of step (a), wherein the receptors for the candidate biomarker, which are grafted to the surface of the core, are loaded with the candidate biomarker protein, a flux of a solution with potential drug, submitting an IR beam through said IR cell, and obtaining an infrared spectrum therefrom; and

(c) analyzing the obtained infrared spectra to evaluate the effect of the potential drug by determining the secondary structure distribution of the soluble candidate biomarker protein in the sample and after application of the potential drug, wherein an upshift or disappearance of the amide I band in the spectrum of (b) relative to (a) is indicative for the efficacy of the potential drug.

According to the invention the infrared transparent material of the IR cell is selected from gallium arsenide, silicon, germanium, zinc selenide and diamond, and preferably is germanium. Further, the candidate biomarker protein undergoes conformational transitions associated with the disease and is an amyloidogenic peptide or a (poly-) peptide of health-status dependent, characteristic secondary structure composition, including Amyloid-beta (Aβ) peptides and Tau protein associated with Alzheimer's disease, alpha-Synuclein associated with Parkinson's disease, Prion protein associated with Creutzfeldt-Jakob disease, or Huntingtin protein associated with Huntington's disease, and preferably is an Aβ peptide or a Tau protein. Moreover, the sample with candidate biomarker protein may be a purified sample of the biomarker or may be a complex body fluid comprising the biomarker including human CSF. Other suitable complex bodily fluids are human serum, blood plasma, lacrimal fluid and nipple aspirate fluid.

It is preferred that said infrared sensor element comprises a germanium internal reflection element being of trapezoid or parallelogram shape and being transparent in the infrared with sufficient signal to noise ratio to detect the amide I band beyond large background absorbance, and at least one receptor for the biomarker protein being antibodies capable of specific and conformational independent binding to the biomarker protein, and being directly grafted to at least one surface, preferably to at least two or three surfaces of said internal germanium reflection element, by silanization with short silane linkers or by thiolation with short thiol linkers, reacting freely accessible amine groups of said at least one receptor with amine-reactive groups on the short silane/thiol linkers, and blocking remaining amine-reactive groups on the short silane/thiol linkers with a blocking substance not cross-reacting with the biomarker protein.

According to the invention it is particularly preferred that the internal reflection element is a germanium monocrystal, preferably is a trapezoid cut germanium monocrystal. It is further preferred that the germanium crystal allows for or provides for one, more than one, or more than three reflections of the infrared light through the reflection element, particularly preferred are more than five reflections or even more than twenty reflections (preferred are 25 reflections with 13 actively sensed reflections). Even more, it is particularly preferred that the internal reflection element is suitable for the parallel analysis by another optical method including detection of fluorescence at different wavelengths. Finally, it is crucial that the blocking substance is not cross-reacting with the biomarker protein, which is selected from casein, ethanolamine, L-lysine, polyethylene glycols, albumins and derivatives thereof. The silane and thiol linkers for the grafting include homogenous silane and thiol linkers, mixtures of silane linkers and mixtures of thiol linkers, and have an effective linker chain length (combined number carbon and heteroatoms) of not more than 20 atoms or not more than 15 atoms, preferably the silane linkers have one of the following formulas:

(i)

(ii)

(iii)

and the thiol linkers have the following formula:

(iv)

wherein W is H or $R^1S$—, X at each occurrence is independently selected from halogen and $C_{1-6}$ alkoxy, n is an integers of 1 to 10, n' is an integer of 1 to 5; $R^1$ at each occurrence is independently selected from $C_{1-6}$ alkyl, Y is selected from a chemical bond, —O—, —CO—, —$SO_2$—, —$NR^2$—, —S—, —SS—, —$NR^2CO$—, —$CONR^2$—, —$NR^2SO_2$— and —$SO_2NR^2$— (wherein $R^2$ is H or $C_{1-6}$ alkyl), and Z is an amine-reactive group including —$CO_2H$, —$SO_3H$ and ester derivatives thereof. The halogen within the present invention includes a fluorine, chlorine, bromine and iodine atom. $C_{1-6}$ alkyl and $C_{1-6}$ alkoxy includes straight, branched or cyclic alkyl or alkoxy groups having 1 to 6 carbon atoms that may be saturated or unsaturated. In case of cyclic alkyl and alkoxy groups, this refers to those having 3 to 6 carbon atoms. Suitable $C_{1-6}$ alkyl and $C_{1-6}$ alkoxy groups include, among others, methyl and methoxy, ethyl and ethoxy, n-propyl and n-propoxy, iso-propyl and iso-propoxy, cyclopropyl and cyclopropoxy, n-butyl and n-butoxy, tert-butyl and tert-butoxy, cyclobutyl and cyclobutoxy, n-pentyl and n-pentoxy, cyclopentyl and cyclopentoxy, n-hexyl and n-hexoxy, cyclohexyl and cyclohexoxy, and so on. The amine-reactive group Z includes all types of functional groups that are reactive with a free amino group. Among those, —$CO_2H$, —$SO_3H$ and ester derivatives thereof (including active esters) are particularly preferred.

The —$(CH_2)_n$— and —$(CH_2)_{n'}$— structural elements in the above formulas may also contain one or more double and/or triple bonds and may be substituted with one or more halogen atoms such as fluorine or with deuterium.

When the infrared sensor element is obtainable by silanization, it is then preferred that in the linkers of formulas (i) to (iii) above X is independently selected from $C_{1-6}$ alkoxy-groups, preferably from methoxy and ethoxy groups, Y is —NHCO—, Z is —$CO_2H$ or an ester derivative thereof, and n is an integer of 1 to 5 and n' is an integer of 1 to 3, preferably n is 3 and n' is 2.

When the infrared sensor element is obtainable by thiolation, it is then preferred that in the linker of formula (iv) above W is H, Y is a chemical bond, Z is —$CO_2H$ or an ester derivative thereof, and n is an integer of 1 to 8 and n' is an integer of 1 to 5, preferably n is 8 and n' is 4.

In a particular preferred embodiment, the biomarker protein is an Aβ peptide and the receptor binding to the Aβ peptide is an antibody, preferably is an antibody specifically binding to the central epitope of the Aβ peptide, including antibody A8978.

In a further particular preferred embodiment, the biomarker protein is a Tau protein and the receptor binding to the Tau protein is an antibody, preferably is an antibody specifically binding to a epitope accessible for all Tau variants (phosphorylated, truncated, 3 to 4 repeat regions etc., isoforms), including antibody Tau-5.

In the method of the invention, the concentration of the potential drug in the solution is either below the detection limit of the IR determination or can be easily subtracted by reference spectra of the potential drug.

In the method of the invention, when the potential drug possesses amide bands, such as antibodies, the method further comprises subtracting a reference spectrum of the potential drug for detecting the shift of the amide I band of the target protein.

In particular, when the target protein is an Aβ peptide, a shift of the amide I band, preferably a shift of the amide I band maximum, to any value indicative for the Aβ peptide secondary structure is indicative for the efficacy of the potential drug. Notably, for a fibrillary fraction of the Aβ peptide a shift from of 1626 $cm^{-1}$ to 1655 $cm^{-1}$ and for the total fraction of the Aβ peptide a shift from 1636 $cm^{-1}$ to 1655 $cm^{-1}$ is indicative for the efficacy of the potential drug.

Further, when the target protein is a Tau protein, a shift of the amide I band, preferably a shift of the amide I band maximum, to any value indicative for the Tau protein secondary structure is indicative for the efficacy of the potential drug. Notably, for a fibrillary fraction of the Tau protein a shift from of 1626 $cm^{-1}$ to 1655 $cm^{-1}$ and for the total fraction of the Tau protein a shift from 1636 $cm^{-1}$ to 1655 $cm^{-1}$ is indicative for the efficacy of the potential drug.

Figure 4:
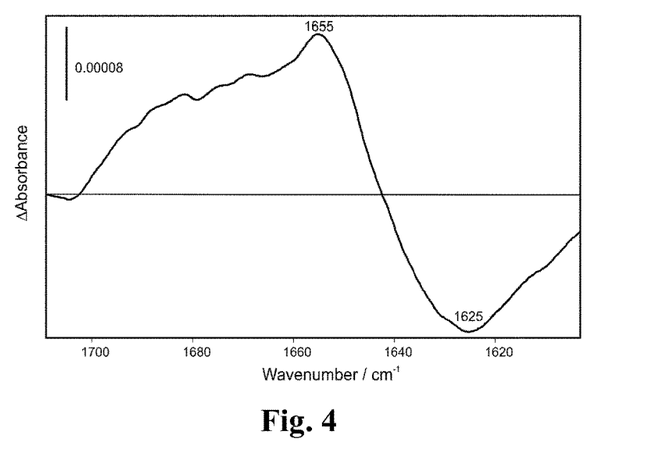
FIG. 4: The difference spectra between the two spectra shown in FIG. 3 shows mainly a decrease of β-sheet and an increase of α-helix induced by addition of methylene blue (50 μM). This shows that the drug intervention on the secondary structure distribution can be monitored by the invention very precisely.
Figure 5:
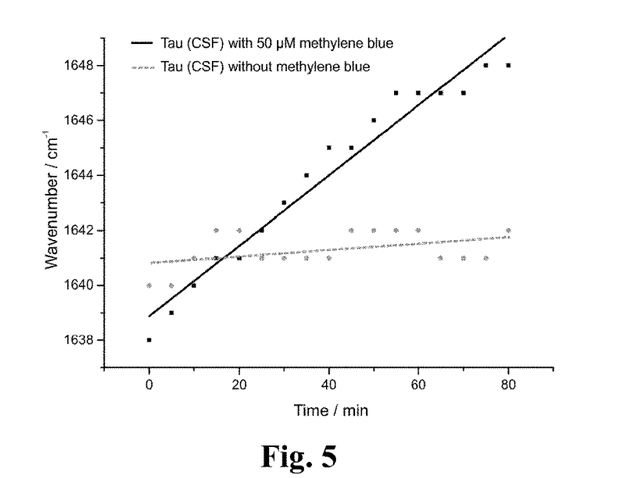
FIG. 5: Structural shift of the amide I band of the Tau protein from CSF with (black) and without the presence of methylene blue (grey) in dependence of time.
Figure 6:
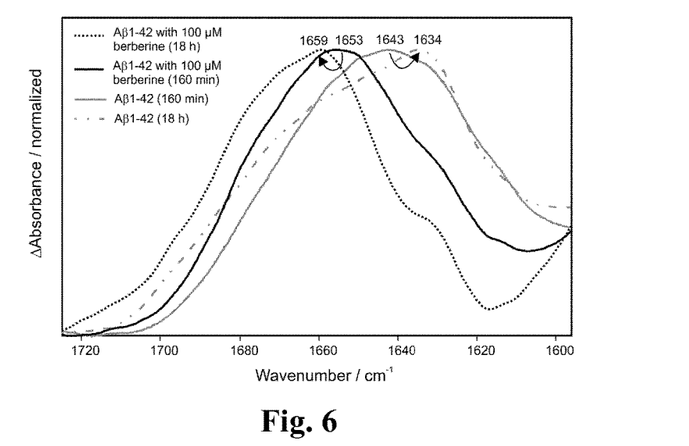
FIG. 6: Aβ$_{1-42}$ protein was immobilized on antibody (A8978) terminated germanium surface. The light grey (right) spectrum shows the a broad distribution of different secondary structures with an absorbance maximum at 1634 cm$^{-1}$ characteristic for fibrillized Aβ$_{1-42}$. Furthermore, the amide I of the intermediate of the folding process (dashed light grey) is shown after 160 min. Addition of the potential drug berberine (100 μM) results in a significant different secondary structure distribution dominated now by an α-helical or mainly monomeric isoform of Aβ$_{1-42}$ at 1659 cm$^{-1}$ (black spectrum, left), however with a significant shoulder at 1634 cm$^{-1}$. The dashed dark grey spectrum shows the amide I band as an intermediate of the folding process after 160 min.

The present invention is based on the detection of secondary structural changes induced by the potential drug by means of vibrational spectroscopy. The invention uses in principle the same experimental set-up as our previous patent application WO 2015121339. Instead of a 70V (Bruker) we employed an 80V FTIR spectrometer (Bruker) to improve the signal to noise ratio of the measurements. As internal reflection element germanium crystal were chemically modified with NHS-silanes, which function as anchors for the covalent attachment of the desired antibodies. After blocking the surface with casein the surface is ready for capturing of the target protein (Tau or $A\beta_{1-42}$). The Tau protein was directly extracted out of human CSF. This is a great advantage since no purified protein samples are required and no pretreatment of CSF is needed, which makes the assay easier accessible for the application in clinics or clinical labs. The target protein was analyzed in the presence of the potential drug and the effect was monitored by the change in the amide I band. As shown for the Tau protein the effect of the potential drug methylene blue was directly monitored (FIG. 3). The change of the secondary structural distribution is characterized by the drug induced shift of the amide I band from 1640 cm$^{-1}$ (untreated) to 1653 cm$^{-1}$ (treated). The effect becomes even more evident in the double difference spectrum (FIG. 4), which clearly shows a negative band at 1625 cm$^{-1}$ indicative for the disappearance of β-sheet and a positive band at 1655 cm$^{-1}$ typical for α-helix. In a control without drug the amide I band absorbance maximum of the Tau protein remains stable (FIG. 5). Thus, for the pre-selection of drug candidates in the treatment of neurodegenerative diseases the invention provides an ideal platform. Another example is the study of the second important biomarker $A\beta_{1-42}$. Since the developed sensor is universal, the antibody A8978 against the epitope 13-28 of $A\beta_{1-42}$ could be applied for the analysis of the potential drug berberine. To monitor a potential effect of berberine the surface was loaded with synthetic $A\beta_{1-42}$. Without any incubation the auto-induced fibrilization process at high concentrations leads to a broad secondary structure distribution of $A\beta_{1-42}$ dominated by β-sheet (FIG. 6, light grey). Addition of berberine shifts the amide I maximum of the broad secondary structure distribution from 1634 to 1659 cm$^{-1}$ indicating mainly α-helical or monomeric species (FIG. 6, black). Thus, berberine seems to decelerate the auto-induced fibrilization process. It may be an interesting target for further investigations. In conclusion, the method provides label-free direct information about the intervention of the secondary structure distribution of the target protein by a drug candidate as demonstrated for Tau and $A\beta_{1-42}$. It resolves the different intervention of the drug on the same target protein. This universal approach can in principle be transferred to any protein and small molecule (potential drug) and has therefore a very high potential for pharmaceutical applications.

The invention is further disclosed in the following Examples, which are however not to be construed so as to limit the application.

EXAMPLES

Materials and Methods:
The same experimental set-up is used as in applicant's previous patent application WO 2015121339.
Sampling and Pretreatment:
CSF was drawn by lumbal puncture and aliquoted at the university hospital Essen, snap-frozen in liquid nitrogen, shipped and stored at −80° C. Samples were not pretreated before the measurement, only thawed at 37° C. for 30 s and kept on ice until used.
Phosphate Buffered Saline (PBS-Buffer):
137 mM sodium chloride (NaCl), 2.7 mM potassium chloride (KCl), 12 mM total-phosphate (in the form of $Na_2HPO_4$ and $NaH_2PO_4$), pH 7.4.
Casein Blocking-Solution:
200 mM sodium hydroxide (NaOH), 1% (w/v) casein from bovine milk (powder), pH adjusted with $H_3PO_4$ to 7.4.

Silanization-Solution:
The used NHS-silane (N-(4,4,4-triethoxysilanebutyl)succinamic acid 2,5-dioxopyrrolidin-1-yl ester) was synthesized and characterized as described (Schartner et al., JACS 135(10):4079-4087 (2013)).
Antibody:
For the analysis of $A\beta_{1-42}$ the antibody A8978 (lot no: 061M4773, Sigma Aldrich) was employed. In case of the Tau protein the antibody Tau-5 (AHB0042, Thermo Fisher Scientific) was used.
$A\beta_{1-42}$:
The human Aβ-peptide was purchased from Sigma-Aldrich (A9810, Amyloid-beta-Protein fragment 1-42).
Potential Drugs:
Methylene blue (methylthionine hydrochloride, lot no: 66720) and berberine chloride (lot no: B3251) were purchased by Sigma Aldrich.
Performing the Measurement:
The general procedure is identical to the patent application WO 2015121339. IR-measurements were performed on a Vertex 80V spectrometer (Bruker Optics GmbH, Ettlingen, Germany) with liquid nitrogen cooled mercury-cadmium-telluride (MCT) detector. Double-sided interferograms were recorded in forward-backward interferometer movement at a 80 kHz data rate with a spectral resolution of 2 cm$^{-1}$, Blackman-Harris-3-Term-apodisation, Mertz-phase correction and 4 times zero filling. Reference spectra were recorded as an average of 1000, sample spectra of 200 interferograms. Recording reference single channel spectra of the blank sensor, sensor with 2-propanol, the silanized surface, the buffers, antibody or casein coated surface in equilibrium states enabled high sensitivity difference spectroscopy based on Lambert-Beer law ($E=-\log(I/I_0)$). The absorbance of the state change is the negative decadic logarithm of the intensity relation before and after the change.
Tau-Protein Treated with Methylene Blue:
The Tau antibody (Tau-5) from Thermo Fisher Scientific was covalently attached to the germanium surface as described for other antibodies by Nabers et al. (Nabers et al., J. Biophotonics 9(3):224-34 doi:10.1002/jbio.201400145 (2016)). After blocking the Tau-antibody terminated surface was incubated with 100 μl of human CSF till the Tau protein was successfully immobilized (about 60 min). In the next step, 2 ml of a 50 μM methylene blue solution (PBS, pH 7.4) was flushed over the surface till the system was equilibrated (1 ml) and then circulated for 60 min. The effect on the secondary structure of tau was directly monitored by the band position and shape of the amide I.
Aβ-Peptide Treated with Berberine:
The antibody A8979 (Sigma-aldrich) was employed for capturing the Aβ-peptide (Nabers et al., Anal. Chem. 88(5): 2755-62 doi:10.1021/acs.analchem.5b04286 (2016)). The Aβ-peptide ($A\beta_{1-42}$, synthetic, Sigma-aldrich, Taufkrichen, Germany) was monomerized by incubation with hexafluoro-2-propanol as described elsewhere (Nabers et al., J. Biophotonics 9(3):224-34 doi:10.1002/jbio.201400145 (2016)). For the analysis 100 μg of $A\beta_{1-42}$ were circulated over the antibody terminated sensor for 1 h to ensure that the drug is not interfering with the immobilization process. In the control experiments the immobilization of $A\beta_{1-42}$ was monitored for further 17 h (total 18 h) in the presence of the potential drug, to follow the auto-induced fibrilization process (FIG. 6, light grey spectrum). To analyze the effect of the potential drug berberine the same protocol as in the control experiment was used. The only difference was the addition of 100 μM berberine after the 1 h immobilization of $A\beta_{1-42}$ (PBS, pH 7.4) by equilibrating with 1.5 mL of 100

μM berberine solution and subsequently circulating the system in the presence of 100 μM berberine (FIG. 6, black spectrum). The effect on the secondary structure of $A\beta_{1-42}$ was directly monitored by the band position and shape of the amide I. The corresponding dashed spectra show intermediates of the folding processes for each experiment after a total time of 160 min.

Pretreatment of the Spectra:

By scaled subtraction of a reference spectrum water vapor was removed. Spectra were baseline corrected, a sliding average was performed as described (Schartner et al., Chembiochem 15(17):2529-34 doi:10.1002/cbic.201402478 (2014)) and normalized to the same amide I signal intensity in the region 1730 till 1590 $cm^{-1}$ depending on the observed secondary structure.

Example 1: Methylene Blue "Cures" Alzheimer's Disease In Vitro

Figure 2:
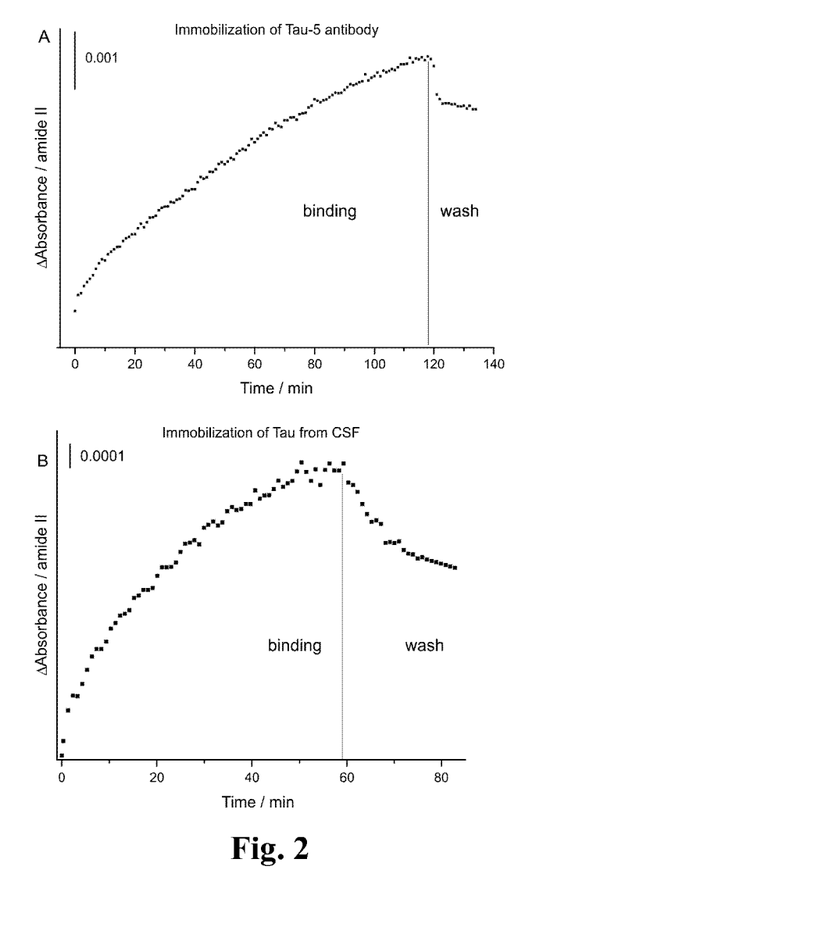
FIG. 2: (A) Binding of the antibody of Tau-5 via silane-chemistry and final wash with PBS buffer. (B) The antibody specifically captures the Tau protein from human CSF, which remains sufficiently stable after washing the surface with PBS buffer.

To monitor the drug effect of methylene blue the invented method was employed. We previously invented an immuno-ATR sensor, which differentiates AD with an accuracy of 90% based on CSF and 84% based on blood plasma analyzes (Nabers et al., Anal. Chem. 88(5):2755-62 doi:10.1021/acs.analchem.5b04286 (2016)). First, we employed silane chemistry to modify the germanium surface (Schartner et al., JACS 135(10):4079-87 doi:10.1021/ja400253p (2013)). Second, the monoclonal IgG1 antibody Tau-5 was covalently immobilized on the germanium surface. The immobilization is completed after 2 hours as presented in FIG. 2A by reaching an absorbance of 5 mOD. After washing the surface with binding buffer 1 the antibody remains stable (FIG. 2A). To obtain a highly specific surface the saturation with casein is crucial (Nabers et al., J. Biophotonics 9(3): 224-34 doi:10.1002/jbio.201400145 (2016)). Finally, a complex sample such as cerebrospinal fluid (CSF) is flushed over the sensor. The resulting monoexponential binding kinetics of the Tau protein is presented in FIG. 2B. With the immobilized Tau fraction it is now possible to analyze the effect of the potential drug methylene blue. A 50 μM solution of methylene blue was flushed over the surface and after equilibration the system was circulated. The above mentioned immuno-ATR-FTIR sensor (WO 2015121339) for the diagnosis of Alzheimer's disease uses for the diagnosis a simple threshold classifier with a value at 1643 $cm^{-1}$ for AD and disease control differentiation, which can also be transferred to the Tau protein (unpublished data, patent application in preparation). The black spectrum in FIG. 3 shows an amide I maximum of 1640 $cm^{-1}$ indicating a higher amount of disease related β-sheet enriched isoforms, which would be diagnosed as diseased by our immuno-IR-sensor (Nabers et al., Anal. Chem. 88(5):2755-62 doi: 10.1021/acs.analchem.5b04286 (2016). Upon methylene blue incubation a significant shift to higher wavenumbers was observed within 1 h (FIG. 3, grey spectrum), thus a secondary structure change to an disordered or α-helical conformation was induced by the potential drug methylene blue. This is in consistence with the in vivo studies of the group of Claude Wischik, which demonstrated the reduction of the Tau associated tangles in the human brain (Šimić et al., Biomolecules 6(1):6 doi:10.3390/biom6010006 (2016); Wischik et al., PNAS 93(20):11213-18 (1996)). The patient would now be diagnosed as healthy by our developed immuno-ATR-FTIR sensor (FIG. 3, grey spectrum) (Nabers et al., Anal. Chem. 88(5):2755-62 doi:10.1021/acs.analchem.5b04286 (2016)). Thus, the presented approach has a very high potential as prescreening tool for the selection of candidate drugs against the AD and also against other neurodegenerative diseases. By subtraction of the drug treated state minus the untreated state the secondary structural change becomes even more obvious as indicated by the negative band at 1625 $cm^{-1}$ and the positive band at 1655 $cm^{-1}$ (FIG. 4). To prove that the changes are really caused by methylene blue a control without methylene was performed (FIG. 5). The amide I maximum is stable and only differs about ±1 wavenumbers without the drug incubation (FIG. 5, grey line), whereas with the presence of the drug a clear shift to higher wavenumbers is observed (FIG. 5, black line).

Example 2: Berberine Decelerates the Aggregation of $A\beta_{1-42}$

The second important marker protein for the Alzheimer's disease is $A\beta_{1-42}$. We analyzed the fibrilization process with the described method. Synthetic $A\beta_{1-42}$ was monomerized with hexafluoro-2-propanol. A solution of monomerized $A\beta_{1-42}$ was flushed over the sensor and specifically immobilized with antibody A8979 (Nabers et al., J. Biophotonics 9(3):234-34 doi:10.1002/jbio.201400145 (2016)). The spontaneous fibrilization was monitored over 18 h resulting in an amide I maximum of 1634 $cm^{-1}$ (FIG. 6, light grey spectrum). The same experiment was done in the presence of 100 μM berberine showing a 25 $cm^{-1}$ shift of the amide I maximum to 1659 $cm^{-1}$ (FIG. 6, black spectrum). This indicates that berberine directly decelerates the aggregation process of $A\beta_{1-42}$. A small amount of β-sheet enriched isoforms is observed as a shoulder at 1634 $cm^{-1}$, but the dominating conformation is monomeric $A\beta_{1-42}$. This suggests a direct interaction of berberine and $A\beta_{1-42}$ that could be applied as drug to prevent the initial processes of AD and thus might be useful to slow down disease progression.

Example 3: Methylene Blue Affects Also $A\beta_{1-42}$

Figure 7:
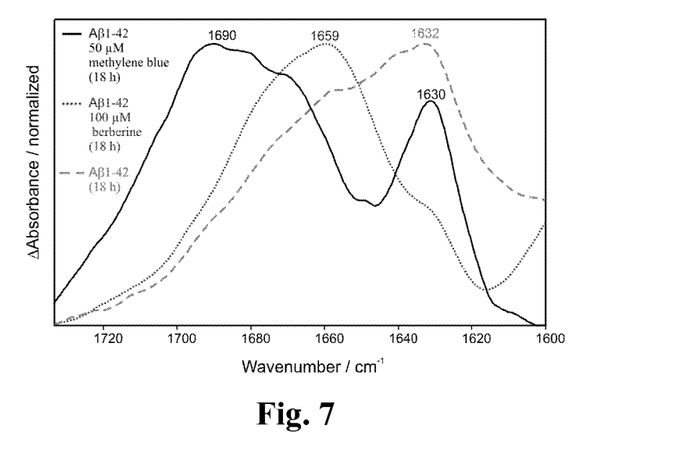
FIG. 7: Comparison of the Aβ$_{1-42}$ secondary structure distribution (black) after incubation with methylene blue (light grey), berberine (grey), and without any drug intervention (black). As seen already in FIG. 6 berberine shifts the distribution mainly to α-helix, whereas methylene blue induces β-sheet and fibril formation. This finding is in consistence with the literature (Necula et al., Biochem. 46(30):8850-60 doi:10.1021/bi700411k (2007). This shows that different interventions on the secondary structure distribution by different drugs can be resolved.

In addition, the effect of methylene blue on $A\beta_{1-42}$ was investigated under the same conditions as for berberine. The obtained spectrum clearly shows a fibril (FIG. 7, light grey spectrum), which is in consistence with the literature (Necula et al., Biochem. 46(30):8850-60 doi:10.1021/bi700411k (2007)). The effect is discussed to prevent the formation of toxic oligomers and therefore might have a potential in treating Alzheimer's disease (Necula et al., Biochem. 46(30):8850-60 doi:10.1021/bi700411k (2007)). This shows that the method works very efficient and gives direct information regarding the molecular mechanism of the drug.

Example 4: Berberine does not Affect Tau

Figure 8:
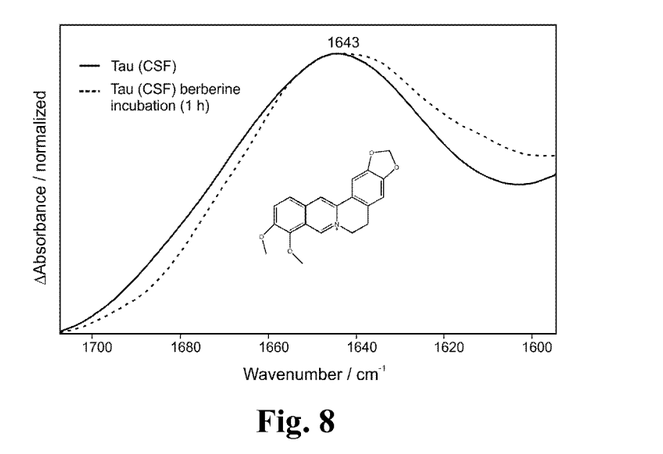
FIG. 8: The potential drug berberine (100 μM) did not change the secondary structure distribution of the Tau protein (extracted from CSF) in contrast to methylene blue as shown in FIG. 3. This finding shows that different interventions of different drugs on the same target protein can be resolved.

Furthermore, we studied the effect of berberine on the Tau protein (from CSF) under the same conditions as for methylene blue (FIG. 8). The amide band and its maximum are not affected by the berberine treatment, which indicates that berberine has no significant effect on the Tau protein in comparison to methylene blue (FIG. 3 and FIG. 8).

The invention claimed is:
1. A drug-screening assay comprising the steps:
    contacting a flux of a sample of a complex body fluid comprising a target protein, wherein the target protein undergoes secondary structure changes associated with a disease, with an infrared (IR) cell comprising an infrared sensor element comprising:

an internal reflection element comprising a core of an infrared transparent material and at least one antibody capable of specific and conformationally independent binding to the target protein, wherein the antibody is covalently attached to at least one surface of said internal reflection element; wherein said contacting loads said at least one antibody with the target protein;

submitting an IR beam through said IR cell; and obtaining a first infrared spectrum therefrom;

contacting the IR cell with a solution comprising a potential drug;

submitting an IR beam through said IR cell; and obtaining a second infrared spectrum therefrom, and subtracting a reference spectrum of the potential drug from the second infrared spectrum; and analyzing: i) the first infrared spectrum and ii) the second infrared spectrum after subtraction of the reference spectrum of the potential drug, to evaluate the effect of the potential drug by determining the secondary structure distribution of the target protein in the sample before and after application of the potential drug, wherein an upshift or disappearance of an amide I band characteristic for β-sheets in the second infrared spectrum after subtraction of the reference spectrum of the potential drug relative to the corresponding amide I band in the first spectrum is indicative of the efficacy of the potential drug; wherein the potential drug is an antibody or comprises amide bonds.

2. The method of claim 1, wherein
(i) the infrared transparent material of the IR cell is independently selected from gallium arsenide, silicon, germanium, zinc, selenide and diamond and/or
(ii) the target protein is an amyloidogenic peptide or a (poly-) peptide of health-status dependent, characteristic secondary structure composition; and/or
(iii) the sample of the complex body fluid with Tau target protein is human cerebrospinal fluid (CSF), serum or blood plasma.

3. The method of claim 1, wherein said infrared sensor element comprises a germanium internal reflection element being of trapezoid or parallelogram shape and being transparent in the infrared with sufficient signal to noise ratio to detect the amide I band, and wherein the at least one antibody is and being directly grafted covalently attached to at least one surface of said internal germanium reflection element by a method comprising:

silanization with short silane linkers or by thiolation with short thiol linkers, reacting freely accessible amine groups of said at least one antibody with amine-reactive groups on the short silane/thiol linkers, and blocking remaining amine-reactive groups on the short silane/thiol linkers with a blocking substance not cross-reacting with the biomarker protein.

4. The method of claim 1, wherein the internal reflection element
(i) is a germanium monocrystal; and/or
(ii) allows for or provides for more than one passages of the infrared light through the reflection element; and/or
(iii) is further suitable for the parallel analysis by another optical method including detection of fluorescence at different wavelengths; and/or (iv) the blocking substance not cross-reacting with the target protein is selected from casein, ethanolamine, L-lysine, polyethylene glycols, albumins and derivatives thereof.

5. The method of claim 3, wherein the silane and thiol linkers comprise homogeneous silane and thiol linkers, mixtures of silane linkers and mixtures of thiol linkers, and have an effective linker chain length (combined number carbon and heteroatoms) of not more than 20 atoms or not more than 15 atoms.

6. The method of claim 1, wherein the target protein is a Tau protein and wherein a shift of the amide I band to any value indicative for the Tau protein secondary structure is indicative for the efficacy of the potential drug.

7. The method of claim 1, wherein the potential drug is for the treatment of a neurodegenerative disease.

8. The method of claim 2, wherein the infrared transparent material is germanium.

9. The method of claim 4, wherein the germanium monocrystal is a trapezoid cut germanium monocrystal.

10. The method of claim 5, wherein the silane linkers have one of the following formulas:

$$X_3Si-(CH_2)_n-Y-(CH_2)_{n'}-Z, \quad (i)$$

$$X_2R^1Si-(CH_2)_n-Y-(CH_2)_{n'}-Z \text{ or} \quad (ii)$$

$$X(R^1)_2Si-(CH_2)_n-Y-(CH_2)_{n'}-Z, \quad (iii)$$

and the thiol linkers have the following formula:

$$WS-(CH_2)n\text{-}Y-(CH_2)n'\text{-}Z, \quad (iv)$$

wherein W is H or $R^1S$—, X at each occurrence is independently selected from halogen and $C_{1-6}$ alkoxy, n is an integers of 1 to 10, n' is an integer of 1 to 5; $R^1$ at each occurrence is independently selected from $C_{1-6}$ alkyl, Y is selected from a chemical bond, O—, —CO—, —SO$_2$—, —NR$^2$—, —S—, —SS—, —NR$^2$CO—, —CONR$^2$—, —NR$^2$SO$_2$— and —SO$_2$NR$^2$— (wherein $R^2$ is H or $C_{1-6}$ alkyl), and Z is an amine-reactive group including —CO$_2$H, —SO$_3$H and ester derivatives thereof.

11. The method of claim 1, wherein the potential drug is an antibody.

12. The method of claim 6, wherein the shift of the amide I band is a shift to the amide 1 band maximum.

13. The method of claim 6, wherein the shift for a fibrillary fraction of the Tau protein from of 1626 cm$^{-1}$ to 1655 cm$^{-1}$ is indicative of the efficacy of the potential drug.

14. The method of claim 6, wherein the shift for the total fraction of the Tau protein from 1636 cm$^{-1}$ to 1655 cm$^{-1}$ is indicative of the efficacy of the potential drug.

15. The method of claim 10, wherein X is independently selected from methoxy and ethoxy groups.

16. The method of claim 10, wherein n is 3 and n' is 2.

17. The method of claim 10, wherein n is 8 and n' is 4.

18. The method of claim 1, wherein
(i) the target protein is an Aβ peptide, or
(ii) the target protein is a Tau protein.

19. The method of claim 1, wherein the target protein is an Aβ peptide and a shift of the amide I band to any value indicative for the Aβ peptide secondary structure is indicative of the efficacy of the potential drug.

20. The method of claim 10, wherein the infrared sensor element is obtainable by:
(A) silanization and in the linkers of formulas (i) to (iii), wherein X is independently selected from $C_{1-6}$ alkoxy-groups, Y is —NHCO—, Z is —CO$_2$H or an ester derivative thereof, and n is an integer of 1 to 5 and n' is an integer of 1 to 3; or (B) thiolation and in the linkers of formula (iv), wherein W is H, Y is a chemical bond, Z is —$CO_2H$ or an ester derivative thereof, and n is an integer of 1 to 8 and n' is an integer of 1 to 5.

21. The method of claim 20, wherein X is independently selected from methoxy and ethoxy groups.

22. The method of claim 20, wherein n is 3 and n' is 2.

23. The method of claim 20, wherein n is 8 and n' is 4.

* * * * *

UNITED STATES PATENT AND TRADEMARK OFFICE
CERTIFICATE OF CORRECTION

PATENT NO. : 11,592,451 B2
APPLICATION NO. : 16/349194
DATED : February 28, 2023
INVENTOR(S) : Klaus Gerwert et al.

Page 1 of 1

It is certified that error appears in the above-identified patent and that said Letters Patent is hereby corrected as shown below:

On the Title Page

In Item (56), under "Other Publications" in Column 2, Line 1, delete "infared" and insert -- infrared --.
In Item (57), under "Abstract" in Column 2, Line 3, delete "targetbiomoiecule," and insert -- target biomolecule, --.
On Page 2, in Item (56), under "Other Publications" in Column 1, Line 5, delete "anti-arnyloidogenic" and insert -- anti-amyloidogenic --.
On Page 3, in Item (56), under "Other Publications" in Column 2, Line 48, delete "Nat'l" and insert -- National --.
On Page 4, in Item (56), under "Other Publications" in Column 2, Line 48, delete "Taupathies:" and insert -- Tauopathies: --.

In the Specification
In Column 2, Line 64, delete "Huntigton" and insert -- Huntington --.
In Column 5, Line 59, delete "the a" and insert -- the --.
In Columns 7-8, Line 67 (Column 7) Line 1 (Column 8), delete "cycloppentoxy," and insert -- cyclopentoxy, --.
In Column 9, Line 56, delete "lumbal" and insert -- lumbar --.
In Column 10, Line 25, delete "-apodisation," and insert -- -apodization, --.
In Column 10, Line 53, delete "Taufkrichen," and insert -- Taufkirchen, --.

In the Claims
In Column 14, Line 43, in Claim 12, delete "amide 1" and insert -- amide I --.

Signed and Sealed this
Second Day of May, 2023

Katherine Kelly Vidal
*Director of the United States Patent and Trademark Office*